(12) United States Patent
Blanchard et al.

(10) Patent No.: US 7,854,235 B2
(45) Date of Patent: Dec. 21, 2010

(54) DENTAL TAPE AND PROCESS FOR OBTAINING A DENTAL TAPE

(75) Inventors: Stephen John Blanchard, Princeton, NJ (US); Emilson Ismael Netto, Jacarei (BR); Daniel Ricardo Queiroz, Sao Jose dos Campos (BR); Francisco Antonio Rimoli, São Paulo (BR)

(73) Assignee: McNeil-PPC, Inc., Skillman, NJ (US)

( * ) Notice: Subject to any disclaimer, the term of this patent is extended or adjusted under 35 U.S.C. 154(b) by 470 days.

(21) Appl. No.: 12/026,839

(22) Filed: Feb. 6, 2008

(65) Prior Publication Data

US 2008/0230087 A1 Sep. 25, 2008

Related U.S. Application Data

(60) Provisional application No. 60/896,029, filed on Mar. 21, 2007.

(51) Int. Cl.
*A61C 15/04* (2006.01)

(52) U.S. Cl. .................................................. 132/321

(58) Field of Classification Search .................. 132/321, 132/329, 323; 433/143; 424/49; 427/2.29; 264/2.5
See application file for complete search history.

(56) References Cited

U.S. PATENT DOCUMENTS

| | | | |
|---|---|---|---|
| 4,450,849 A | 5/1984 | Cerceo et al. |
| 4,646,766 A | 3/1987 | Stallard |
| 4,776,358 A | 10/1988 | Lorch |
| 4,836,226 A | 6/1989 | Wolak |
| 4,941,487 A | 7/1990 | VanBeneden |
| 4,996,056 A | 2/1991 | Blass |
| 4,998,978 A | 3/1991 | Varum |
| 5,209,251 A | 5/1993 | Curtis et al. |
| 5,226,435 A | 7/1993 | Suhonen et al. |
| 5,293,886 A | 3/1994 | Czapor |
| 5,357,989 A | 10/1994 | Gathani |
| 5,357,990 A | 10/1994 | Suhonen et al. |
| 5,413,127 A | 5/1995 | Hill |
| 5,518,012 A | 5/1996 | Dolan et al. |
| 5,588,452 A | 12/1996 | Peck |
| 5,657,779 A | 8/1997 | Blass et al. |
| 5,806,539 A | 9/1998 | Blass et al. |
| 5,865,197 A | 2/1999 | Bible et al. |
| 5,875,797 A | 3/1999 | Chiang et al. |
| 5,967,154 A | 10/1999 | Anderson |
| 6,003,525 A | 12/1999 | Katz |

(Continued)

FOREIGN PATENT DOCUMENTS

DE 199 08 238 A 8/2000

(Continued)

*Primary Examiner*—Cris L Rodriguez
*Assistant Examiner*—Vanitha Elgart

(57) ABSTRACT

Monofilament dental tapes including a core body having first and second opposing external faces, where at least one of the external faces has a plurality of indentations protruding into the core body of the dental tape, where the plurality of indentations are provided in from about 5% to about 95% of the total area of the first or second external faces, the indentations having a depth within the core body corresponding to from about 0.1% to about 95% of the thickness of the core body, taken transversally to the external face containing the plurality of indentations.

14 Claims, 9 Drawing Sheets

U.S. PATENT DOCUMENTS

| | | |
|---|---|---|
| 6,016,816 A | 1/2000 | Ariagno |
| 6,251,410 B1 | 6/2001 | Schiraldi et al. |
| 6,340,027 B1 | 1/2002 | Hagne et al. |
| 6,371,133 B1 | 4/2002 | Gant |
| 6,453,912 B1 | 9/2002 | Antler |
| 6,527,996 B2 | 3/2003 | Schiraldi et al. |
| 6,536,448 B2 | 3/2003 | McDevitt et al. |
| 6,545,077 B2 | 4/2003 | Hill et al. |
| 6,575,176 B1 | 6/2003 | Hill et al. |
| 6,591,844 B2 | 7/2003 | Barlow et al. |
| 6,604,534 B2 | 8/2003 | Hill |
| 6,609,527 B2 | 8/2003 | Brown |
| 6,672,316 B1 | 1/2004 | Weihrauch |
| 6,742,528 B2 | 6/2004 | Dave |
| 6,884,309 B2 | 4/2005 | Schweigert |
| 6,907,889 B2 | 6/2005 | Brown |
| 6,916,880 B2 | 7/2005 | Hill et al. |
| 7,055,530 B2 | 6/2006 | Husted |
| 7,281,541 B2 | 10/2007 | Lorch |
| 2002/0081550 A1 | 6/2002 | Karazivan |
| 2002/0083956 A1* | 7/2002 | Hill .......................... 132/321 |
| 2002/0104548 A1 | 8/2002 | Bhupendra |
| 2003/0041873 A1 | 3/2003 | Contratto |
| 2005/0279378 A1 | 12/2005 | Lorch |
| 2006/0016457 A1 | 1/2006 | Hoffman, III |
| 2006/0112968 A1 | 6/2006 | Brown et al. |
| 2006/0237028 A1 | 10/2006 | Hamidy |
| 2006/0243297 A1 | 11/2006 | Brown |
| 2009/0120455 A1* | 5/2009 | Ochs et al. .................. 132/329 |

FOREIGN PATENT DOCUMENTS

| | | |
|---|---|---|
| WO | WO 99/45820 A | 9/1999 |
| WO | WO 02/44448 A | 6/2002 |

* cited by examiner

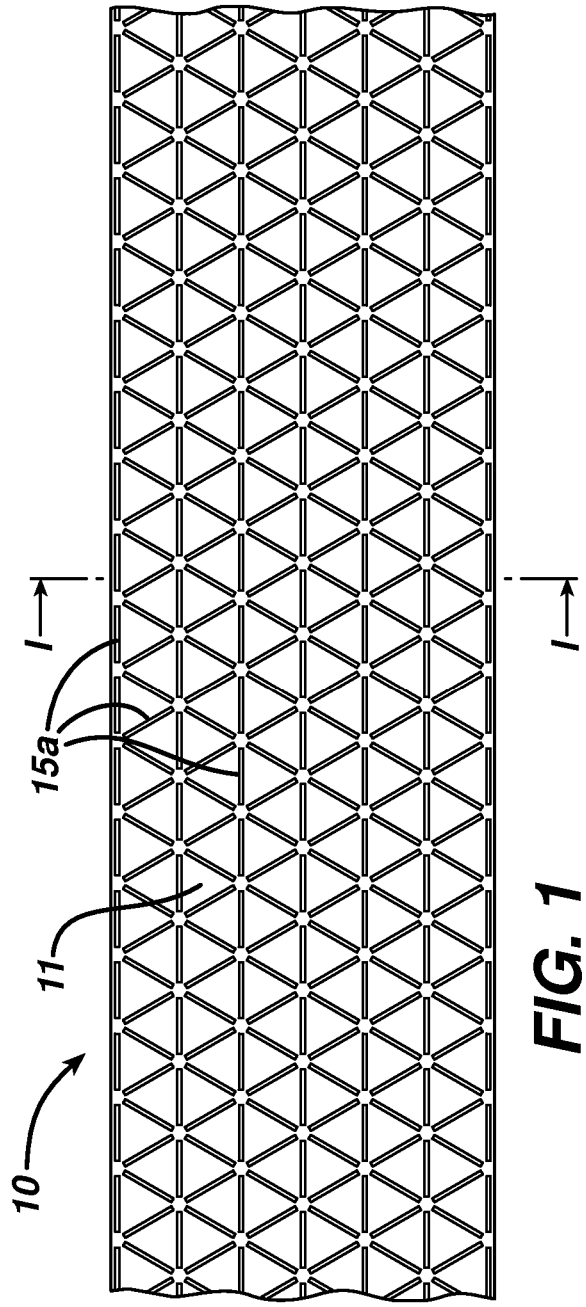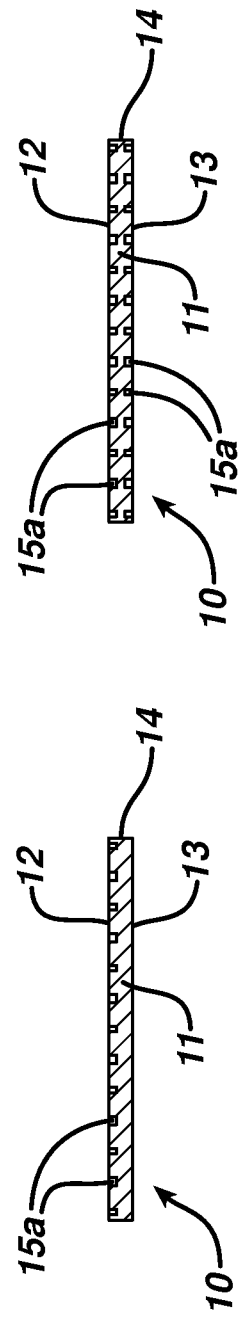
FIG. 1
FIG. 1A
FIG. 1B

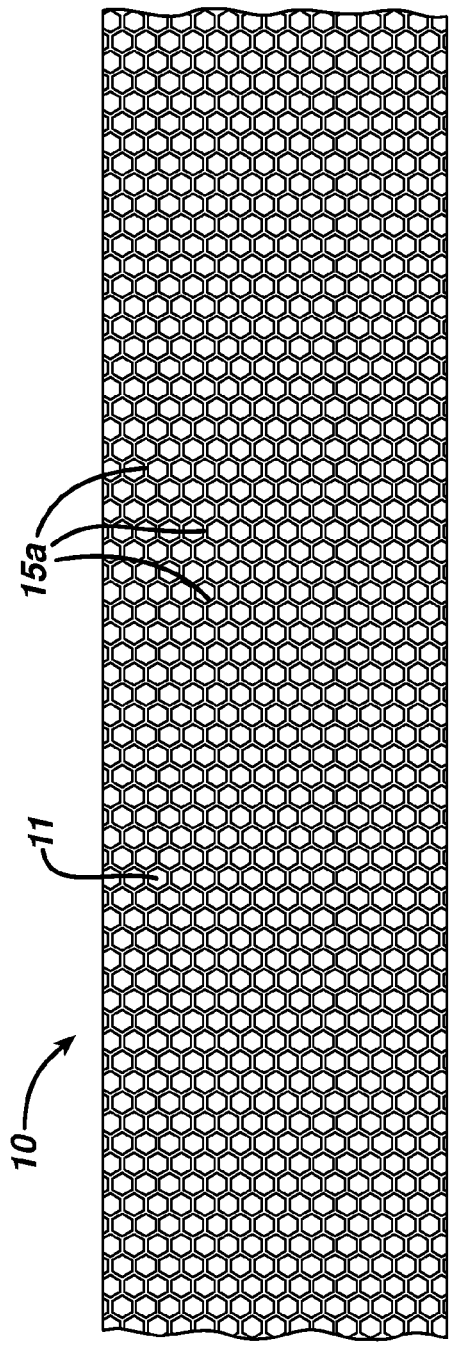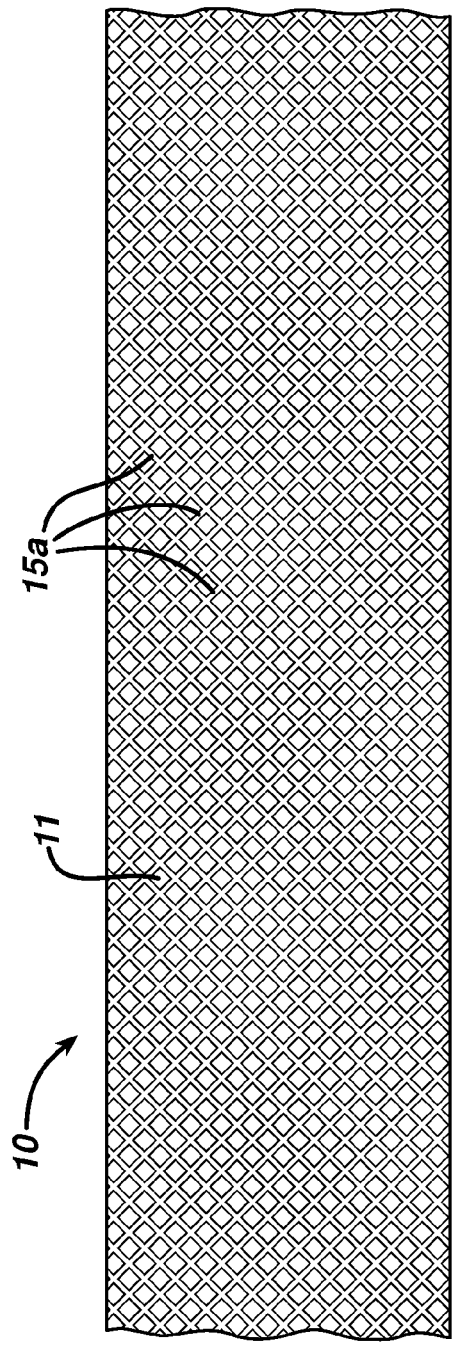

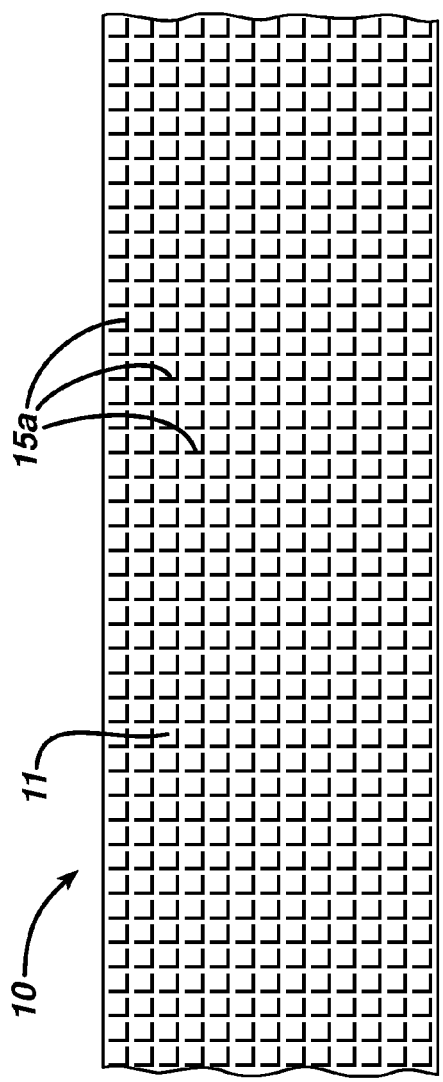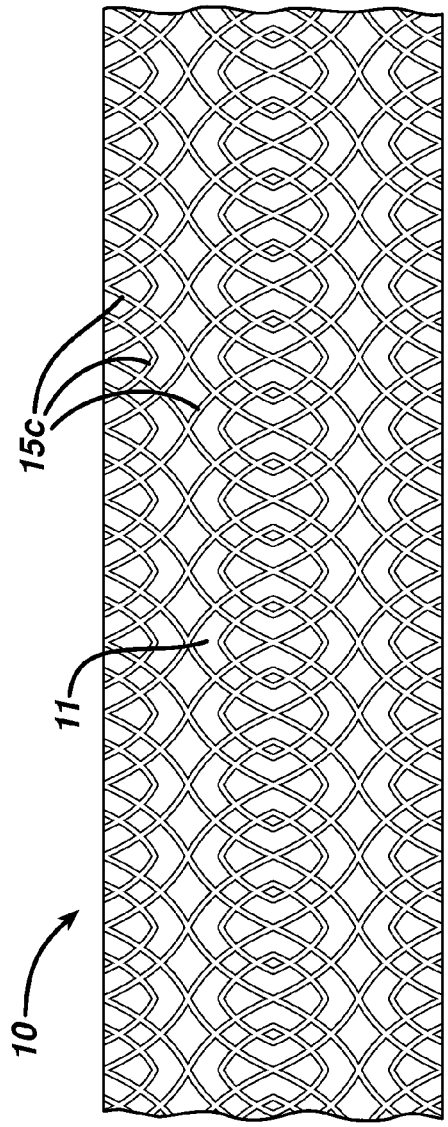
FIG. 4
FIG. 5

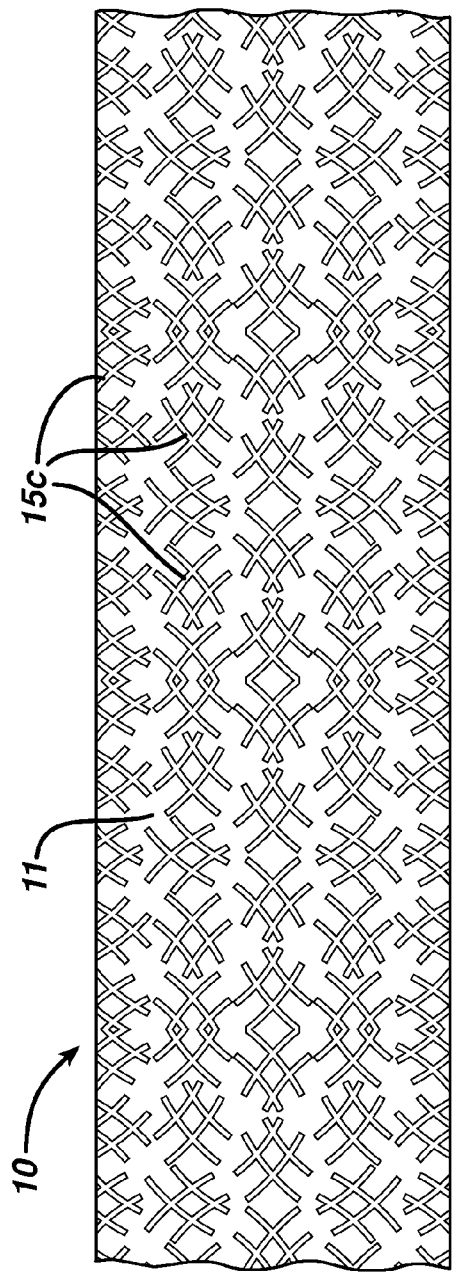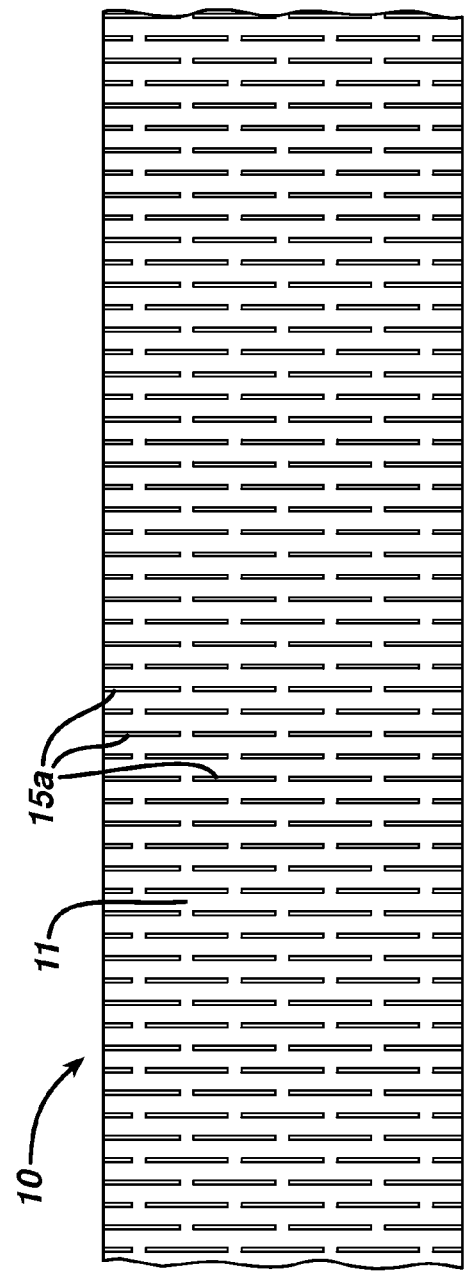

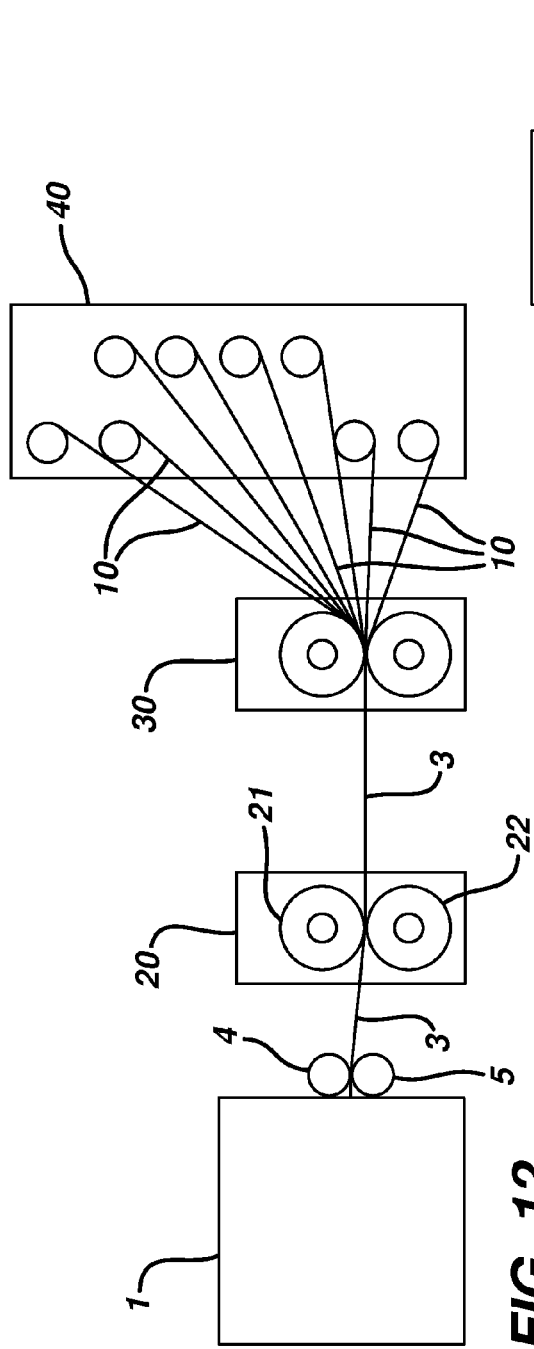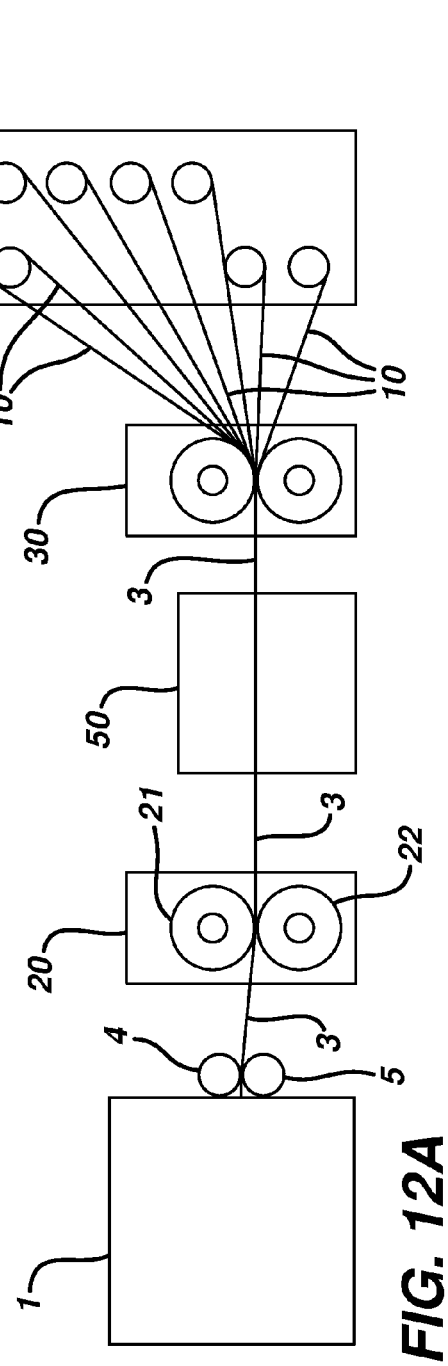

DENTAL TAPE AND PROCESS FOR OBTAINING A DENTAL TAPE

This application claims the benefit of provisional application 60/896,029 filed on Mar. 21, 2007.

FIELD OF THE INVENTION

This invention refers to a monofilament dental tape to be used as an interdental cleaning means, to remove bio-film (plaque) and food residues from the interdental spaces and a process for obtaining such monofilament dental tape.

BACKGROUND OF THE INVENTION

The dental flosses formed by multiple filaments that are held together as a strand during their manual application in the interdental spaces are well known in the prior art. With the friction movement of the floss against the proximal walls of the teeth, the different filaments are progressively disaggregated or separated from one another, promoting a greater capacity of removing the food residues by the dental floss.

These multifilaments are held together until they are rubbed in the interdental spaces. Although they are widely used and easy to insert in the interdental spaces these multifilament dental flosses have the inconvenience of allowing the separation or disaggregation of the multifilaments during the rubbing or scraping operation in the dental surfaces, causing discomfort to the user, which shall be as great as the indentations of the user's teeth.

In addition to the inconvenience above, these multifilament dental flosses require the provision of relatively high amounts of binding agents. However, excessive amounts of binding agents may impair, at a higher or lower degree, the pliability characteristic of the flosses during the application in the interdental spaces, and they also require more raw materials per length unit.

Another construction of these interdental supplementary cleaning elements is defined by the known dental tapes, of rectangular cross-section, formed by a monofilament generally obtained from a film extruded from plastic material, such as polyolefin, polyamide, polyester and fluoropolymers such as polytetrafluoroethylene (PTFE). Because they are monofilament and, therefore, united, these tapes do not have the inconvenience of tending to separate or fray when rubbed in the interdental spaces.

The known monofilament dental tapes have a smaller surface area in comparison to the interstitial surface area of the multifilament dental flosses. The smaller surface area reduces the capacity or efficacy of removing the biofilm and residues from the interdental spaces. Also, the reduced surface area, in interstitial terms, of these known monofilament dental tapes, reduces their capacity of aggregating binding agents to operate as vehicles for the incorporation of additives with abrasive, bactericide, flavoring functions, etc. In addition, because they are smooth, these monofilament dental tapes have grasping characteristics that are still poor and do not provide the user with the feeling that they are properly retained in the fingers during flossing.

The known monofilament dental tapes, with a smooth surface, have the characteristic of accepting only relatively reduced amounts of binding agents, in the form of light surface coatings consisting of, for example, different waxes having known gripping enhancing properties. The restrictions imposed by said smooth monofilament tapes to the amount of binding agents to be used in the formation of the surface coating lead to undesirable limitations in the amount of additional additives, with different active functions, such as flavoring, abrasive, bactericide, etc., to be carried by the binding agent.

A smooth dental floss having a friction enhancing wax-based surface coating, for example microcrystalline wax, to increase the gripping of the dental floss and also to operate as a carrier for different additives having active functions, is disclosed in U.S. Pat. No. 5,209,251. In such smooth dental flosses, particularly in monofilament dental flosses, the surface coating made of a binding agent is fundamental to allow imparting to the dental floss adequate gripping and also a desired capacity of rubbing and removing residues by means of additives having abrasive function, carried by the surface coating. The limitations in the amount of binding agent that can be stably incorporated to the tape undesirably restrict the efficiency of the surface coating in its function as a carrier of additives with active functions.

U.S. Pat. No. 4,646,766 (the '766 patent) discloses a dental tape constituted by a certain length of a monofilament of incipiently/slightly fibrillatable plastic film obtained from, e.g. a polypropylene film. Such films are coherent films that fibrillate spontaneously on rubbing against the surface of a tooth, and include films that have already been fibrillated and rendered temporarily stable. In this constructive solution, described in the '766 patent, the embossing operation to which the plastic tape is subjected is defined and adjusted with the purpose to provide the tape with the property to fibrillate or disaggregate in a reduced and pre-determined level, when subjected to the friction in the interdental spaces. Although such fibrillation increases the capacity of removing biofilm (plaque) and residues, such fibrillation inside the interdental spaces contribute to discomfort by the user.

In addition to the inconvenience related to the fibrillation, this prior art polymeric tape has the same disadvantages mentioned before regarding the monofilament tapes, as regard their limitations in the amount of surface binding agent which can be adequately and stably incorporated to the tape, in order to act as a gripping enhancing means and also as a carrier for additives with abrasive, flavoring, bactericide functions, etc.

U.S. Pat. No. 5,657,779 describes a method and a device to form elongated PTFE films, particularly for formation of dental tapes. The method described aims to produce a PTFE dental tape that reduces or avoids the tape fibrillation during its use and easily receives various coatings, for example, a wax carrying other additives, such as abrasives, bactericides, flavoring agents, etc. Although fibrillation is reduced during use, this prior art monofilament dental tape, with surface area limited to the cross section contour, also has the disadvantage of requiring the application of a surface binding agent to increase gripping, but in an amount which may constitute a limitation to the amount of different additives to be carried by the surface binding agent.

As noted above, while monofilament dental tapes are known, there still exists a need for monofilament dental tapes that are easily inserted into interdental spaces, provide improved gripping by the user, provide improved application and retention of additives to the tapes, with or without known binding agents, and maintain comfort by the user by avoiding fibrillation, all without compromising physical mechanical properties. The dental tapes of the present invention provide such characteristics.

SUMMARY OF THE INVENTION

The present invention includes monofilament dental tapes that comprise a core body having a first external face and a second external face opposite the first external face, wherein at least one of the first and second external faces comprises a plurality of indentations protruding into the core body of the dental tape. The plurality of indentations are provided in from about 5% to about 95% of the total area of the at least one of the first and second external faces. The indentations have a depth within the core body, in relation to the at least one of the first and second external faces comprising the plurality of indentations, corresponding to from about 0.1% to about 95% of the thickness of the core body, taken transversally to the at least one of the first and second external faces comprising the plurality of indentations.

BRIEF DESCRIPTION OF THE DRAWINGS

The invention shall be described below, referencing the attached drawings, as examples of possible embodiments of the invention and in which:

FIG. 1 represents a side plan view of a longitudinal extension of a dental tape of the present invention;

FIG. 1A represents a magnified cross section of the dental tape illustrated in FIG. 1, taken according to line I-I in FIG. 1, where one of the first and second external faces comprises a plurality of indentations protruding into the core body;

FIG. 1B represents a magnified cross section of a dental tape similar to that illustrated in FIG. 1, where both the first and second external faces comprise a plurality of indentations protruding into the core body;

FIGS. 2 to 11 represent side plan views of longitudinal extensions of various embodiments of dental tape according to the present invention;

FIG. 12 represents a process diagram, illustrating, in a simplified manner, the basic operations involved in the dental tape formation in an "on-line" process, from a film obtained in polymeric material, with a width superior to that of the dental tape to be taken to the consumer, up to the winding of each individual dental tape before being conducted to its final package;

FIG. 12A represents a diagram similar to the one in FIG. 12, to illustrate a variant of the process according to which the dental tape is subjected, after the embossing operation, to a coating operation;

DETAILED DESCRIPTION OF THE INVENTION

Figure 8:
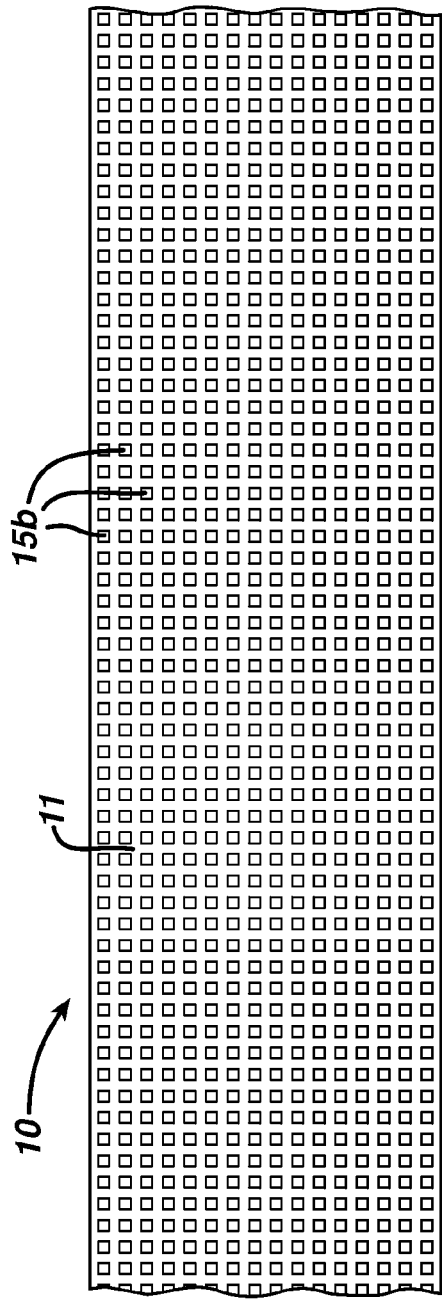

The present invention provides a non-stretchable monofilament dental tape that can be easily obtained from an extruded plastic film. The dental tapes provide high mechanical strength and present good properties of pliability, easiness to be grasped by the user and also improved capacities of removing plaque and residues from the interdental spaces, without the occurrence of fibrillation in the monofilament in relation to the same characteristics of a similar monofilament tape without said indentations.

The invention also provides a monofilament dental tape that has a substantial increase in the surface area and the capacity to anchor a surface coating that may be required to provide the dental tape with functions other than those of interdental cleaning, such as flavoring, bactericide, abrasive, sensate, sialagogue, coloring, aromatizing, therapeutical, etc., in relation to the same characteristics of a similar monofilament tape without said indentations.

The general construction described above provides a monofilament dental tape of compact and smooth structure, which is pleasant to the touch, offers great grasping characteristics to the user and which presents a high capacity of removing biofilm and residues from the interdental spaces, due to the provision of indentations, which anchoring capacity allows an optional binding agent to be "stably" associated with the substrate of the dental tape.

As it has been previously stated, the present invention has the purpose to provide a dental tape 10, formed from a plastic film, preferably PTFE, through a simple and relatively low-cost process, which allows the production of a dental tape with good properties of cleaning, gripping, surface coating anchoring, and pliability.

Although PTFE is one of the preferred materials for the formation of the dental tape, it should be understood that other polymeric materials may be used, such as polyolefins, polyamides and polyesters, to be extruded for the formation of any continuous monofilament with polygonal cross section but which, in the attached drawings, is exemplarily defined as rectangular or substantially rectangular, having a core body with two opposite external faces, where the thickness of the core body is substantially inferior to its width. The core body may have an aspect ratio of greater than about 5:1, or greater than about 10:1.

As schematically illustrated in FIG. 12, the polymeric material is processed in an extruding unit 1, which allows the extrusion of a plastic film 3 in the form of a strip, with a width, in the transverse direction, usually corresponding to the sum of the widths of a plurality of dental tapes, to be obtained and provided to the end user.

In the illustrated example, the plastic film 3 is passed through a cooling roll 4 and a directing roll 5 to be fed to an embossing unit 20 which, in the embodiment illustrated in FIG. 12, is defined by a pair of embossing rolls 21, 22 comprising but not limited to hardened steel.

The plastic film 3 should be fed to the embossing unit 20 under a certain tension, preferably free of folds and twists.

In the dental tape 10 exemplarily illustrated in FIGS. 1 and 1A, only one of the external faces 11, 12 is subjected to an embossing operation. In this case, only the upper roll 21 is laterally provided with radial elements, preferably in a slight high relief (not illustrated) to be pressed against the confronting external face of the plastic film 3, while the other roll 22 has a smooth lateral surface, optionally heated, over which the external face of the plastic film 3 is passed.

It should be understood herein that if it is desired to emboss the two opposed external faces 12 and 13 of the dental tape 10, as shown in FIG. 1B, both rolls 21, 22 of the embossing unit 20 should have their lateral surface configured to act against the confronting face of the plastic film 3, producing the desired embossing thereon.

As illustrated in FIG. 12, the plastic film 3, already embossed, is then directed to a cutting device 30, of any known construction and designed to cut longitudinally the plastic film 3 in multiple dental tapes 10, each one defined by a monofilament of the desired width, presenting opposed longitudinal edges. Each dental tape 10 is then individually wound in a winding device 40 with capacity to wind, simultaneously and separately, a plurality of dental tapes 10 cut from the embossed plastic film 3.

Figure 13:
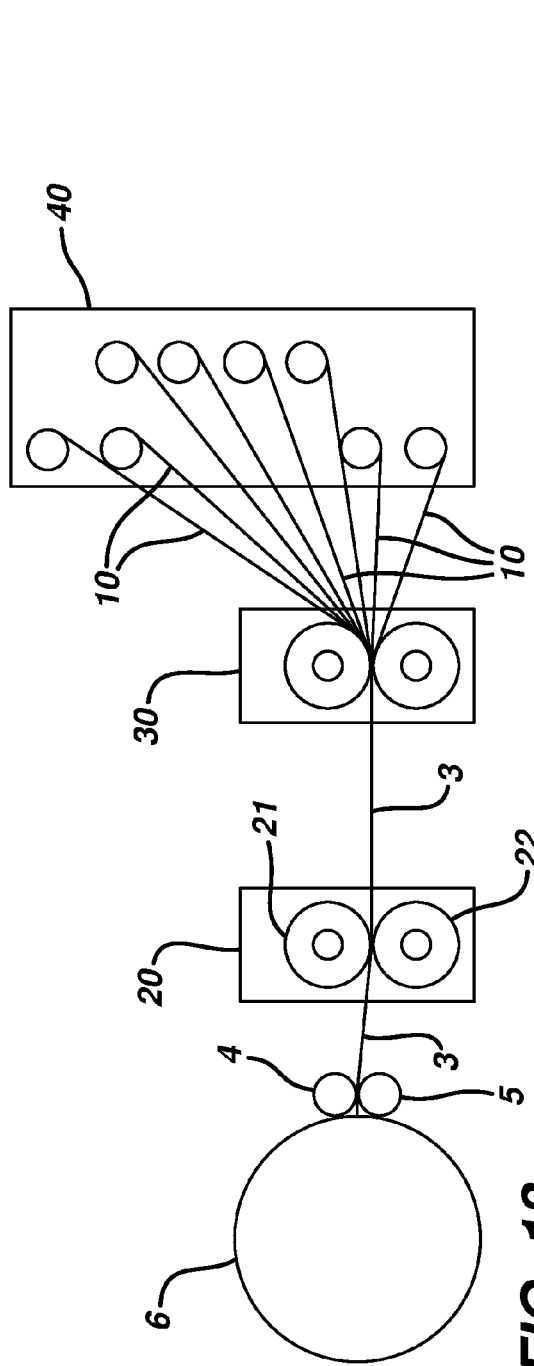
FIG. 13 represents a process diagram illustrating, in a simplified manner, the basic operations involved in dental tape production in an "off-line" process, from a polymeric material film coil with a thickness larger than the dental tape to be taken to the consumer.

The diagram of FIG. 13 illustrates a procedure which differs from the one of FIG. 12 only due to the process for obtaining the dental floss initiates from a coil 6 containing a film of the desired polymeric material, presenting the thickness of the dental floss to be formed, but having a width which generally corresponds to the sum of the widths of a plurality of dental flosses to be obtained. In this example, the process for obtaining the dental floss is an "off-line" process.

Figure 13A:
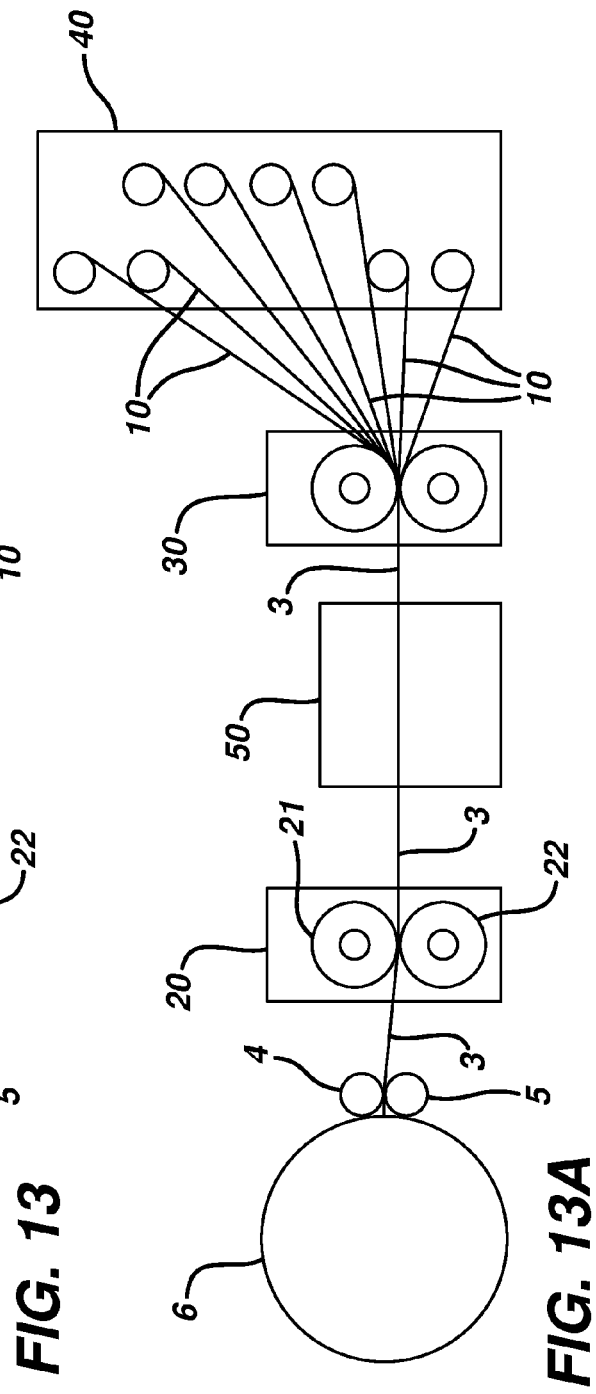
FIG. 13A represents a diagram similar to the one in FIG. 13, illustrating a variant of the process according to which the dental tape is subjected, after the embossing operation, to a coating operation.

FIGS. 12A and 13A illustrate a variant of the system and the process represented in FIGS. 12 and 13, according to which the plastic film 3, already embossed, is directed to a coating applying device 50, of any known construction, to coat the plastic film 3 with at least one binding agent, defining a substrate for carrying at least one additive having an active function, for example selected from flavoring agents, a sensate, a sialagogue, coloring agents, aromatizing agents, therapeutically active agents, abrasive agents, remineralizers, bactericides, etc. After the passage through the coating applying device 50, the plastic film 3 is directed to the cutting device 30, in which it is longitudinally cut in multiple dental tapes 10 with a desired final width defined between opposed longitudinal edges.

Figure 13B:
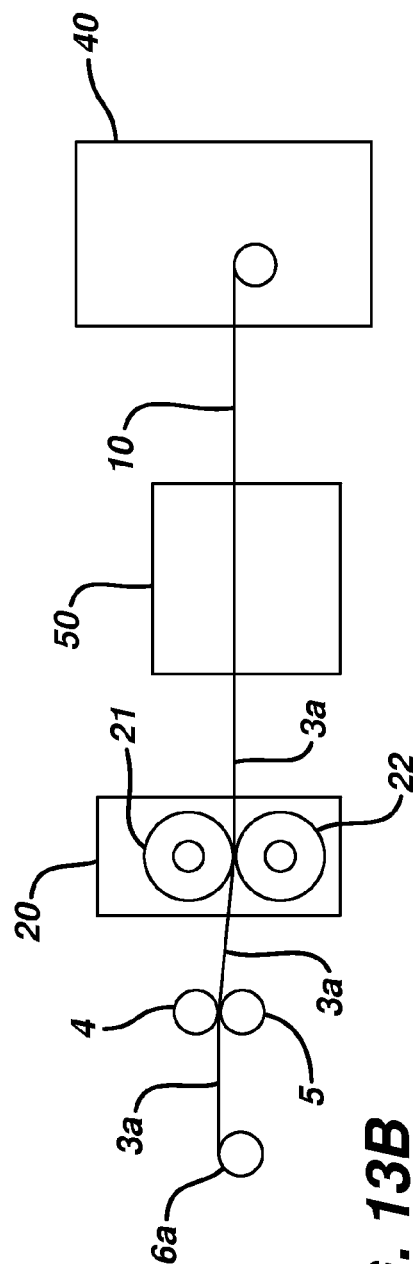
FIG. 13B represents a diagram similar to that of FIG. 13A, illustrating a variant of the process according to which a tape in polymeric material, already cut in the final width to be taken to the consumer, is supplied from a coil in order to be embossed, optionally coated and wound, to be then conducted to an individual package.
Figure 14:
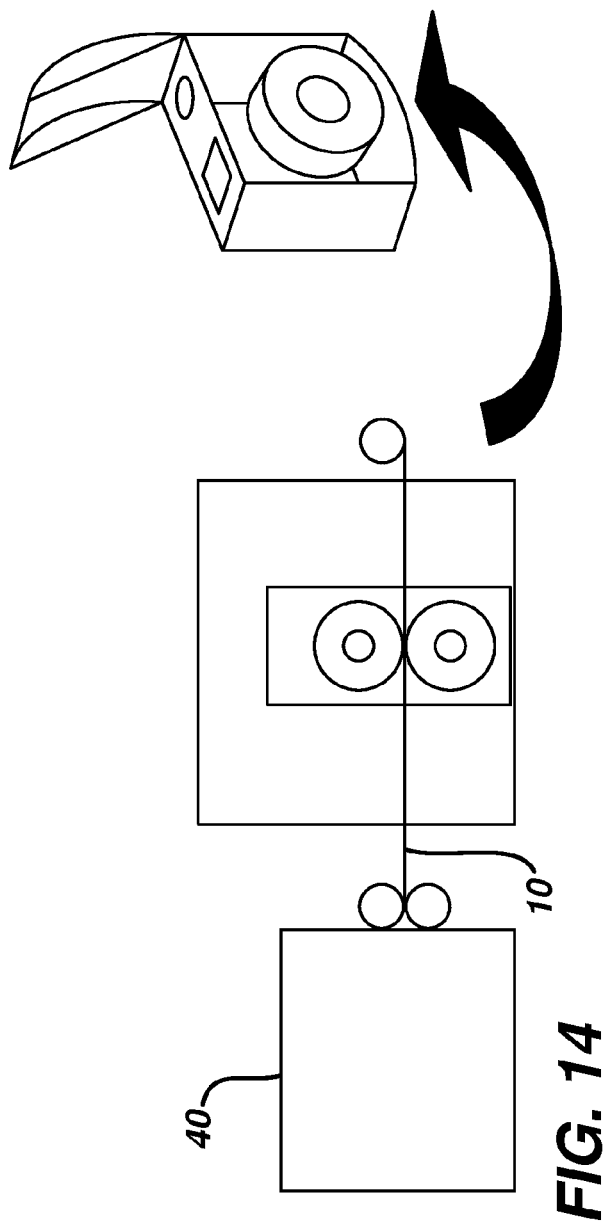
FIG. 14 represents a process diagram illustrating, in a simplified manner, a way to pack the obtained dental tape.

FIG. 13B illustrates a possible way of conducting the process for obtaining the dental tape, starting from a coil 6a containing a film 3a formed from the selected polymeric material and presenting a width which corresponds to the width of the dental tape to be obtained. The film 3a, already cut in the final width and supplied to the present process in a coil 6a, is conducted to the embossing unit 20 and, optionally, to the coating applying device 50, to be then wound in a winding device 40.

FIGS. 1 and 1A exemplify an embossing pattern applied only to one external face 12 of monofilament dental tape 11 and that provides external face 12 with a plurality of indentations in external face 12 of monofilament 11 protruding into core body 14 of dental tape 11.

In the embodiments illustrated in FIGS. 1, 1A and 2-11, indentations are present over substantially the entire transverse width of monofilament 11, in which they are applied. However, it should be understood that, even with the substantial occupation of the width of monofilament 11 by indentations, it is possible that indentations occupy non-continuous longitudinal extensions of each respective dental tape 10 situation in which there would be portions of the longitudinal length of these tapes that are not occupied by indentations. Thus, indentations are provided in about 5% to about 95% of the surface area of external face 12 of monofilament dental tape 11, in which they are embossed.

It may still be observed in FIGS. 1 to 11 that indentations present, in a plan view, an individual area which, together with the number of indentations per surface area unit of the tape, leads to a ratio between the total area of the indentations and the surface area of the tape face portion in which said indentations are provided, of about 5% to about 95%.

It was also observed that indentations should present a depth within the core body, in relation to the tape surface in which they are provided, corresponding from about 0.1% to about 95%, or from about 0.1% to about 50% of the thickness of the tape 3, 3a, taken transversally to said tape surface. These indentations allow the surface area of the monofilament 11 to be considerably enlarged, which increases its capacity of anchoring coatings to be applied onto the dental tape 10, as shall be explained ahead.

Indentations may have different shapes, as exemplarily illustrated in FIGS. 1-11. As can be seen from the figures, the indentations may be arranged spaced apart from one another or in groups, with the indentations of each group being connected to each other. In some arrangements, as those illustrated in FIGS. 1, 2, 3 and 5, the groups of indentations are connected to each other.

In FIG. 1, indentations take the form of small rectilinear grooves 15a that are positioned in a triangular arrangement. In FIGS. 2 and 3, indentations, also in the form of rectilinear grooves 15a, are positioned in a hexagonal and in a lozenge arrangement, respectively. FIGS. 4-8 illustrate other physical arrangements for the indentations provided in the core body of the dental tape, from at least one of the faces thereof having gripping and abrasive functions in the cleaning operation of the dental tape. However, it should be understood that different polygonal configurations may be applied to the contour and to the arrangement of such indentations, and it is important to properly dimension them to provide not only an improved cleaning characteristic to the dental tape structure, but also a significantly increased anchoring capacity to retain functional additives such as flavoring agents, coloring agents, aromatizing agents, therapeutically active agents, abrasive agents, remineralizing agents, bactericide agents, etc., allowing the adhesion of these additives to the monofilament structure to be performed preferably with the use of a known binding agent in the form of a surface coating for the tapes or even the direct application of said additives, with active functions, in the indentations.

FIGS. 1, 2, 3, 5 and 6 illustrate arrangements according to which the indentations, still in the form of rectilinear (15a) and curved (15c) grooves, present mutual intersection regions along the width and length of external face 12 of dental tape 10.

Depending on the shape and the arrangement of indentations, their minimum and maximum dimensions may vary in order to guarantee the desired level of gripping, cleaning, pliability and surface coating anchoring.

As shown in FIGS. 1 and 3, indentations are arranged to form groups, at least part of indentations of the groups being rectilinear and longitudinally aligned in a direction that intersects opposed longitudinal edges of external face 12.

In the arrangement exemplified in FIGS. 2, 4 and 6, indentations of each group of indentations form angles between each other. In FIG. 5, indentations are defined by continuous non-rectilinear grooves 15c, which present mutual intersection regions.

Figure 9:
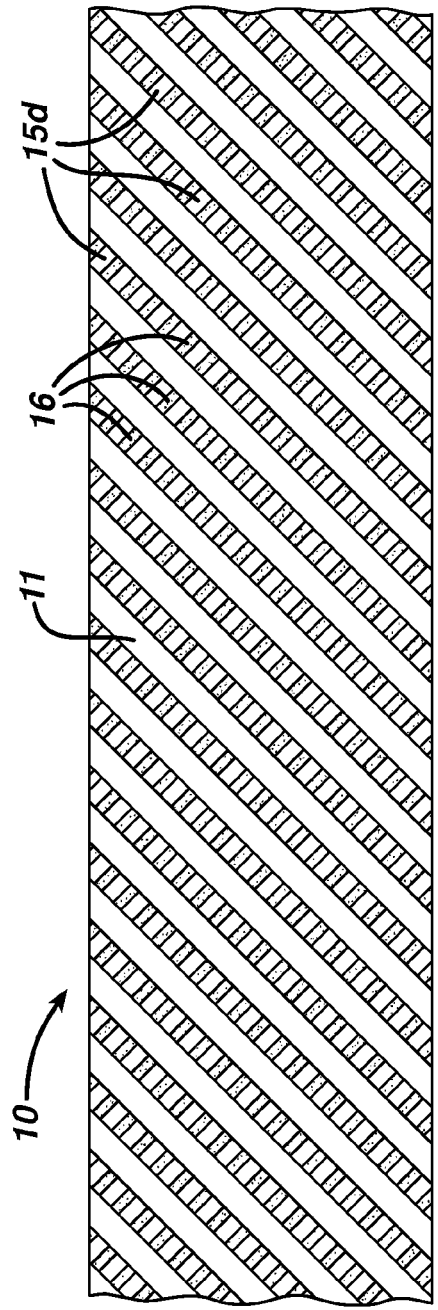
Figure 10:
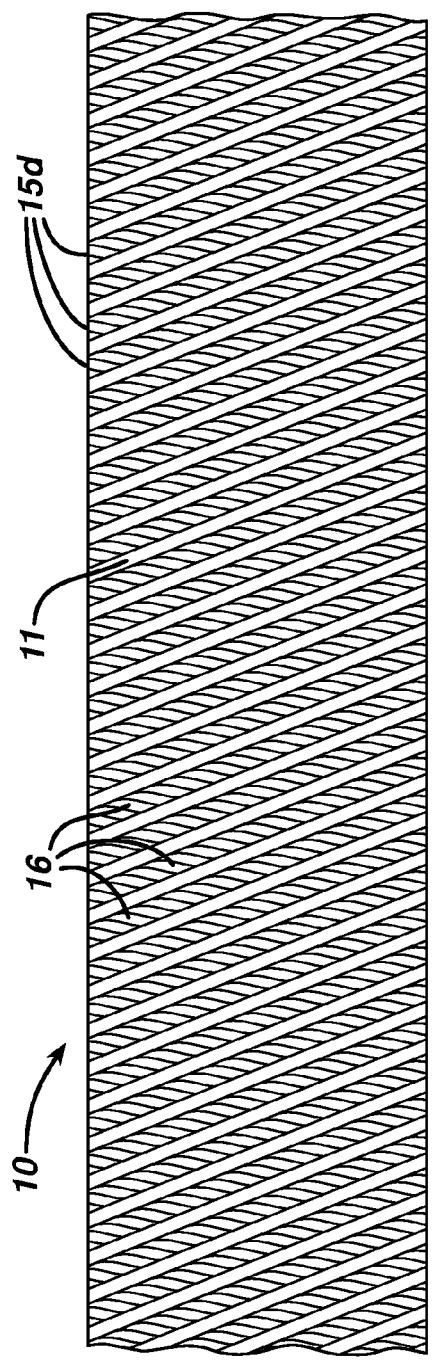

FIGS. 9 and 10 illustrate arrangements according to which indentations are defined by rectilinear and parallel grooves 15d extended in a direction inclined in relation to the longitudinal axis of the dental tape. In FIG. 9, each groove 15d is internally provided, within its depth, with a plurality of spaced apart ribs 16, arranged in a direction that is transversal to the longitudinal axis of the respective groove 15a. Similarly, each groove 15a illustrated in the construction of FIG. 10 is internally provided, within its depth, with parallel ribs 16a inclined in relation to the longitudinal axis of groove 15d.

Figure 11:
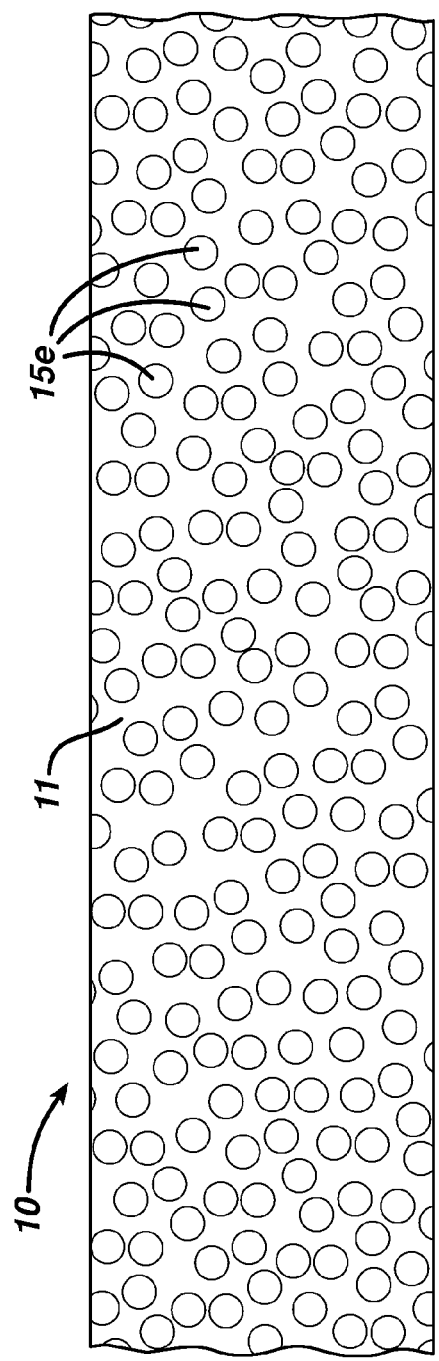

FIG. 11 illustrates an arrangement in which indentations are defined by spaced apart semi-spherical recesses 15e provided along at least part of the width and length of external face 12 of dental tape 10 on which they are provided. FIG. 8 illustrates an arrangement in which indentations are defined by spaced apart polygonal recesses 15b provided along at least part of the width and length of external face 12 of dental tape 10 on which they are provided.

It should be observed that, independently of the design given to the indentations, they should be preferably configured to provide recesses in relation to the external face of the dental tape and also between their internal different surface portions, if existing.

The dimensioning and the configuration of indentations should be made so as to provide not only excellent gripping and cleaning characteristics in the dental tape, regardless the use of a binding agent and different additives with active functions, but also a high level of pliability to the product to be handled by the user.

As illustrated in FIGS. 1 to 11, provided only as non-limiting examples, indentations may be parallel to one another or have mutual intercession regions, defining the most diverse drawings on the monofilament external face on which they are formed. The indentations may be provided in order to occupy, each of them, the whole width of the monofilament 11 that defines the tape 10, or only part of its width, in which situation the combination of different mutually intersecting indentations, makes the whole width of the respective monofilament 11 provided with said indentations.

With the construction mentioned above, the dental tape presents surface elements, defined by the indentations, which although providing dental tape with a greater cleaning capacity, also allow the tape to be superficially and externally coated with a binding agent with the function to define a carrier to which different additives, such as the ones mentioned hereinbefore, may be properly mixed. Due to the greater anchoring capacity of the dental tapes proposed herein, they may carry a substantially greater quantity of a binding agent in relation to the smooth monofilament tapes, to ensure the aggregation of additives with active functions to the dental tape, allowing the proportion of these active additives in the mixture, with the carrier defined by the binding agent, to be much higher, whereby the dental tapes may carry, if desired, more additives with active functions, not impairing the desired high level of pliability of said dental tapes and considerably increasing the capacity to release more intensively the functional additives in the interdental spaces during the dental tape application.

With the advantage mentioned above, resulting from the great anchoring capacity produced by the indentations and, optionally by the projections, the binding agent in the dental tape may comprise from about 0.1% to about 40% of the mass of the monofilament without impairing pliability.

Although it has been so far described an embossing process by means of cylindrical steel rolls 21 and 22, it should be understood that the embossing of the monofilament 11 may be performed by other means, different than the mechanical means defined above. For example, the surface embossing of the plastic film 3 for the posterior formation of monofilament 11 may also be performed by ultrasound or even laser, using known techniques in these areas.

The invention also refers to a process for the formation of the dental tape discussed above, from the same extruded plastic monofilament film, to be posteriorly longitudinally divided into multiple tapes, each of them with a width corresponding to the dental tape to be sold to the consumer.

According to a way of carrying out the invention, the present process comprises the basic initial step of subjecting the plastic film 3, extruded from a polymer selected from the group previously defined in this disclosure, to an embossing operation, in order to provide a plurality of indentations 15 in at least part of the extension of an external face of the plastic film 3, which defines at least part of the cross section contour of the dental tape 10 to be formed.

The already embossed film is then longitudinally divided in multiple dental tapes 10, each presenting a width corresponding to the width of the dental tape 10 to be formed.

Optionally, the already embossed dental tape 10 is coated with at least one additive with an active function, selected from the group consisting of anti-plaque agents, bactericide agents, flavoring agents, sensates, sialagogues, coloring agents, aromatizing agents, therapeutically-active agents, abrasive agents and remineralizing agents, in order to deposit and anchor said at least one additive in said indentations 15, and then wind the dental tape obtained, as schematically illustrated in FIGS. 12 and 12A.

As already mentioned, FIGS. 13 and 13A illustrate a variant of the process for obtaining the dental tape which differs from that defined in FIGS. 12 and 12A, only in that it initiates from a plastic film 3 already previously extruded and stored in a coil 6 (off-line process).

In the illustration in FIG. 13B, the process is initiated from a monofilament tape 3a presenting a width corresponding to that of the dental tape 10 to be obtained.

The following examples are provided to exemplify certain embodiments of the invention but are not intended to limit the scope of the inventions.

Example 1

Dental Tape Formation

A series of monofilament dental tapes with a variety of surface indentations were processed as discussed below. For all tapes, the polymer used was polytetrafluoroethylene (PTFE). The PTFE was supplied as a powder and was converted into a tape by an extrusion process. The steps were as follows:

1) The PTFE was stored under 19° C. and 40 percent Relative Humidity (RH).

2) Blending lubricant and filler were added to create a batch.

3) The batch was stored for about 24 hours for ageing prior to extrusion.

4) The batch was extruded to form a ribbon in a vertical extrusion process through a flat die.

5) Once extruded, the ribbon was calendered, dried and stretched to obtain PTFE tape with desired density and geometrical characteristics.

The PTFE ribbon was embossed by a mechanical embossing process. The mechanical embossing process can be a cold or hot nip provided by a pair of rolls; one provided with male protuberances and another provided with female recesses.

For hot mechanical processing, the rolls were heated under an individual temperature control. The temperature ranges can vary from 50° C. to 200° C. or even higher depending on the polymer from which the tape is made. The gap between rolls can vary from 0.01 mm to the tape thickness. The pressure between rolls can vary from 500 to 1,500 Mpa. The male or female rolls can be made from steel or rubber. If made from steel, the hardness shall be from 30 to 60 HRC, if made from rubber, from 50 to 100 shore A.

For cold mechanical processing, the rolls were not temperature controlled. The gap between rolls can vary from 0.01 to the tape thickness. The pressure between rolls can vary from 500 to 1,500 Mpa. The male or female rolls can be made from steel or rubber. If made from steel, the hardness shall be from 30 to 60 HRC, if made from rubber, from 50 to 100 shore A.

Example 2

Dental Tape Pliability

The pliabilities of several of the monofilament dental tapes made in Example 1 were determined by the following pliability test method. Note that all samples were taken from the same lot of material.

First, three specimens of 10 centimeters length were collected from a dispenser containing a sample of the desired dental tape. In each case, the first 50 centimeters at the beginning of the dental tape dispenser were discarded, as were 50 centimeters in between specimens. Then, 0.10-gram weights were fixed at both ends of each specimen. Next, each specimen was hung on a horizontal metallic pin having a diameter of 0.65 millimeter, so that both pending ends of each specimen were exactly the same distance from the metallic pin. The specimens were left to acclimate for two hours under preset conditions (22° C./50% RH). At this point, digital pictures were taken of the each specimen. The distance (d) between the pending "legs" of each specimen were measured in three different points spaced by 1 mm, at 20 mm below the metallic pin and using Leyca Qwin image analyzing software.

The distance (d) between the ends of each specimen being tested is the parameter used to evaluate the dental tape flexibility (or resistance to flexion). The greater the distance between the ends of the specimen, the higher its resistance, and therefore less flexible the product is.

The pliability test mentioned above was applied to dental tapes of the present invention having no embossing at all (Control), and the embossing patterns exemplified in FIGS. 2, 3, 9, 10, and 11 of the accompanying drawings. The pliability results are shown in Table 1 below:

TABLE 1

Pliability Results

| Figure Number | Embossing Pattern | Pliability Distance (d) (mm) | Standard Deviation |
|---|---|---|---|
| Control | No embossing | 7.24 | 0.58 |
| FIG. 2 | Honeycomb | 6.16 | 0.53 |
| FIG. 3 | Indented | 4.86 | 0.14 |
| FIG. 9 | Diagonal | 5.25 | 0.41 |
| FIG. 10 | Jeans/Entangled | 5.57 | 0.83 |
| FIG. 11 | Leather | 7.00 | 0.46 |

As can be seen from Table 1 above, the embossing provided by the present invention leads to an increase in the pliability of the dental tape, that is, to a substantial reduction in the pliability distance of the embossed samples versus the unembossed control. With the exception of the "leather" embossing pattern, all embossing patterns resulted in statistically significant decreases in pliability distance of the embossed samples versus the unembossed control.

Example 3

Dental Tape Friction

The small surface area of PTFE monofilament, as well as low surface tension and/or low coefficient of friction are responsible for poor performance in terms of biofilm removal in the interdental area when it is used as dental floss. A friction test was conducted to compare the embossed polytetrafluoroethylene (PTFE) tapes of the current invention with an unembossed control.

The test method was conducted using a Dynamometer type CRE, brand INSTRON, model 5869, in which two diabolo-shape pins were adapted to work as friction points for the dental tape. The test conditions were as follows:

1. 20±2° C. and 65±4 percent R.H;
2. Initial distance between fixed grip and the first friction pin: 250 mm;
3. First and second friction point arranged at approximately 45°;
4. Distance between friction pins: 115 mm;
5. Weight: 50 grams;
6. Test speed: 300 mm/min;
7. Displacement: 180 mm;
8. Sample length: 650 mm;
9. Five (5) specimens tested for each sample.

The load cell measured the friction force of each dental tape surface against the two diabolo-shaped pins.

The friction test mentioned above was applied to dental tapes of the present invention having no embossing at all (Control), and the embossing patterns exemplified in FIGS. 2, 3, 9, 10, and 11 of the accompanying drawings. The results are shown in Table 2 below:

TABLE 2

Coefficient of Friction Results

| Figure Number | Embossing Pattern | Force (N) | Standard Deviation |
|---|---|---|---|
| Control | No embossing | 0.81 | 0.08 |
| FIG. 2 | Honeycomb | 0.95 | 0.06 |
| FIG. 3 | Indented | 0.89 | 0.06 |
| FIG. 9 | Diagonal | 1.00 | 0.03 |
| FIG. 10 | Jeans/Entangled | 0.97 | 0.04 |
| FIG. 11 | Leather | 0.91 | 0.01 |

Surprisingly, there is a significant increase in friction force after embossing process and consequently the embossed products are expected to have better performance in terms of mechanical removal of biofilm and/or food debris in the interdental space as well as have a better grip (or be less slippery) when compared with control (without embossing).

Example 4

Mechanical Properties of Dental Tape (Based on Test Method ISO 2 062/1993)

The tensile strength and elongation of embodiments of the embossed polytetrafluoroethylene (PTFE) tapes of the current invention were compared with an unembossed control. The test conditions were as follows:

1. 20±2° C. and 65±4 percent R.H;
2. Distance between gauges: 250 mm
3. Speed: 250 mm/min
4. Sample length: 400 mm; and
5. Five specimens were tested for each sample.

The tensile strength and elongation test mentioned above was applied to dental tapes of the present invention having no embossing at all (Control), and the embossing patterns exemplified in FIGS. 2, 3, 9, 10, and 11 of the accompanying drawings. The results are shown in Table 3 below:

| Figure Number | Embossing Pattern | Maximum Force (N) | Elongation (%) @ Max. Force |
|---|---|---|---|
| Control | No embossing | 15.76 ± 0.14 | 7.44 ± 0.31 |
| FIG. 2 | Honeycomb | 16.93 ± 0.19 | 5.30 ± 0.43 |
| FIG. 3 | Indented | 15.89 ± 0.16 | 8.33 ± 1.45 |
| FIG. 9 | Diagonal | 16.44 ± 0.21 | 4.75 ± 0.22 |
| FIG. 10 | Jeans/Entangled | 15.35 ± 0.10 | 8.15 ± 0.41 |
| FIG. 11 | Leather | 16.32 ± 0.11 | 11.49 ± 2.02 |

Surprisingly, the embossing process does not compromise the tensile strength of the tapes of this invention when compared to control (without embossing), which makes it suitable to be used as dental floss.

The ability of embossed polytetrafluoroethylene (PTFE) dental tapes to hold coatings was measured to determine the stability of coatings on the tapes.

A 1-inch wide PTFE sheet with a density of 1.2-1.7 grams/cm$^3$, a denier of 1000-17000, and a thickness of 1.4-2.4 mils was using the "Honeycomb" pattern (see FIG. 2) at 2 different intensities. A sample without embossing was used as a control. All samples were coated with adhesive H2669 from Bostik Findley (Wauwatosa, Wis.) lot AS6081405 targeting 21 grams/m$^2$ and covered with siliconized paper to avoid adhesive loss during handling until further testing.

The samples were then tested (n=10) for peel force according to following steps:
1. Cut a 15-cm sample of coated substrate;
2. Remove siliconized paper;
3. Weight sample;
4. Place a 100% cotton cloth on top of sample;
5. Compress cloth against coated substrate. An automatic system was used to apply a standard weight (2230 gram) along sample's length at constant speed (12"/minuet). Compressing procedure was conducted once;
6. Place final sample (PTFE-Adhesive-Cloth) in Peel equipment;
7. Measure force to completely peel cloth off; and
8. Weight sample.

The average peel force and adhesive loss for the samples are shown on Table 4 below:

TABLE 4

Results of Peel Force Test.

| Sample | Peel Force (kgF) | Adhesive Loss (%) |
|---|---|---|
| Control | 0.533 | 26.00 |
| Embossing | 0.474 | 9.62 |
| Embossing | 0.497 | 3.37 |

The Table shows the peel force for both embossed samples was lower than that of the control. The indentations resulting from the embossing process allow the adhesive to penetrate below the surface of the tape. So, the amount available to bind to the cotton cloth was reduced, and the bonding with cotton cloth was weaker. The table also shows significantly higher adhesive loss for the control when compared to either of the embossed flosses.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

The invention claimed is:

1. A dental tape, comprising:
a monofilament comprising a core body having a first external face and a second external face opposite said first external face, said monofilament having a thickness and width suitable for use as said dental tape,
wherein at least one of said first or second external faces comprises a plurality of indentations protruding into said core body, said plurality of indentations provided in from about 5% to about 95% of the total area of said at least one of said first or second external faces, and wherein each of said indentations has a depth within said core body, in relation to said at least one of said first or second external faces comprising said plurality of indentations, corresponding to from about 0.1% to about 95% of the thickness of said core body, taken transversally to said at least one of said first or second external faces comprising said plurality of indentations.

2. The dental tape of claim 1 wherein said plurality of indentations are present over substantially the entire width of said dental tape.

3. The dental tape of claim 1 wherein said plurality of indentations occupies non-continuous longitudinal extensions of said dental tape.

4. The dental tape of claim 1 further comprising a coating comprising a binding agent.

5. The dental tape of claim 4 wherein said coating comprises an additive having an active function.

6. The dental tape of claim 1 wherein said indentations are in a form selected from the group consisting of polygonal, rectilinear, non-rectilinear, ovular, elliptical and circular.

7. The dental tape of claim 1 wherein each of said first and second external faces comprises said plurality of indentations.

8. The dental tape of claim 7 wherein the surface area of each of said first and second external faces occupied by said plurality of indentations is from about 5% to about 95%.

9. The dental tape of claim 8 wherein said plurality of indentations are present over substantially the entire width of said dental tape.

10. The dental tape of claim 9 wherein said plurality of indentations occupies non-continuous longitudinal extensions of said dental tape.

11. The dental tape of claim 8 wherein said indentations are in a form selected from the group consisting of polygonal, rectilinear, non-rectilinear, ovular, elliptical and circular.

12. The dental tape of claim 8 further comprising a coating comprising a binding agent.

13. The dental tape of claim 12 wherein said coating comprises an additive having an active function.

14. The dental tape of claim 1 comprising a polymer selected from the group consisting of polyolefines, polyamides, polyesters and fluoropolymers.

* * * * *